United States Patent
Terada et al.

(10) Patent No.: US 8,947,776 B2
(45) Date of Patent: Feb. 3, 2015

(54) SUCTION APPARATUS, SEMICONDUCTOR DEVICE OBSERVATION DEVICE, AND SEMICONDUCTOR DEVICE OBSERVATION METHOD

(75) Inventors: Hirotoshi Terada, Hamamatsu (JP); Hiroyuki Matsuura, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 238 days.

(21) Appl. No.: 13/701,035

(22) PCT Filed: Jun. 21, 2011

(86) PCT No.: PCT/JP2011/064172
§ 371 (c)(1),
(2), (4) Date: Nov. 30, 2012

(87) PCT Pub. No.: WO2011/162261
PCT Pub. Date: Dec. 29, 2011

(65) Prior Publication Data
US 2013/0088714 A1 Apr. 11, 2013

(30) Foreign Application Priority Data
Jun. 23, 2010 (JP) .............................. P2010-142868

(51) Int. Cl.
| G02B 21/26 | (2006.01) |
| G01N 21/95 | (2006.01) |
| H01L 21/683 | (2006.01) |
| H01L 21/687 | (2006.01) |
| G01N 21/01 | (2006.01) |
| H01L 21/66 | (2006.01) |

(52) U.S. Cl.
CPC ........ *G01N 21/9501* (2013.01); *H01L 21/6838* (2013.01); *H01L 21/68757* (2013.01); *H01L 21/68785* (2013.01); *G01N 21/01* (2013.01); *H01L 22/12* (2013.01)
USPC .......................................................... 359/391

(58) Field of Classification Search
USPC .......................................................... 359/391
See application file for complete search history.

(56) References Cited

U.S. PATENT DOCUMENTS

| 6,475,398 | B2 * | 11/2002 | Kitahata ........................... 216/2 |
| 7,092,069 | B2 * | 8/2006 | Schuster ........................... 355/53 |
| 7,864,437 | B2 * | 1/2011 | Komatsu et al. .............. 359/661 |
| 8,436,631 | B2 * | 5/2013 | Chua et al. ................ 324/756.01 |

(Continued)

FOREIGN PATENT DOCUMENTS

| JP | 2004-327773 | 11/2004 |
| JP | 2007-324457 | 12/2007 |

(Continued)

*Primary Examiner* — Frank Font
(74) *Attorney, Agent, or Firm* — Drinker Biddle & Reath LLP

(57) ABSTRACT

A suction unit 10 includes a main body portion having a first surface 13 on which a semiconductor wafer W is arranged and a second surface 14 opposite to the first surface 13, and in which a through-hole 15 that penetrates through the first surface 13 and the second surface 14 is formed and a light transmitting portion having a light incident surface 16 and a light emitting surface 17, and which is fitted to the through-hole 15. Further, in the first surface 13, a first suction groove 13a for vacuum sucking the semiconductor wafer W to fix the semiconductor device D to the light incident surface 16 is formed, and in the second surface 14, a second suction groove 14a for vacuum sucking the solid immersion lens S to fix the solid immersion lens S to the light emitting surface 17 is formed.

12 Claims, 14 Drawing Sheets

(56) References Cited

U.S. PATENT DOCUMENTS

2008/0259446 A1* 10/2008 Komatsu et al. .............. 359/391
2010/0039117 A1*  2/2010 Jacobs ......................... 324/537

FOREIGN PATENT DOCUMENTS

| | | |
|---|---|---|
| JP | 2008-141207 | 6/2008 |
| WO | 2006/077834 | 7/2006 |

* cited by examiner

Fig.2
(a)
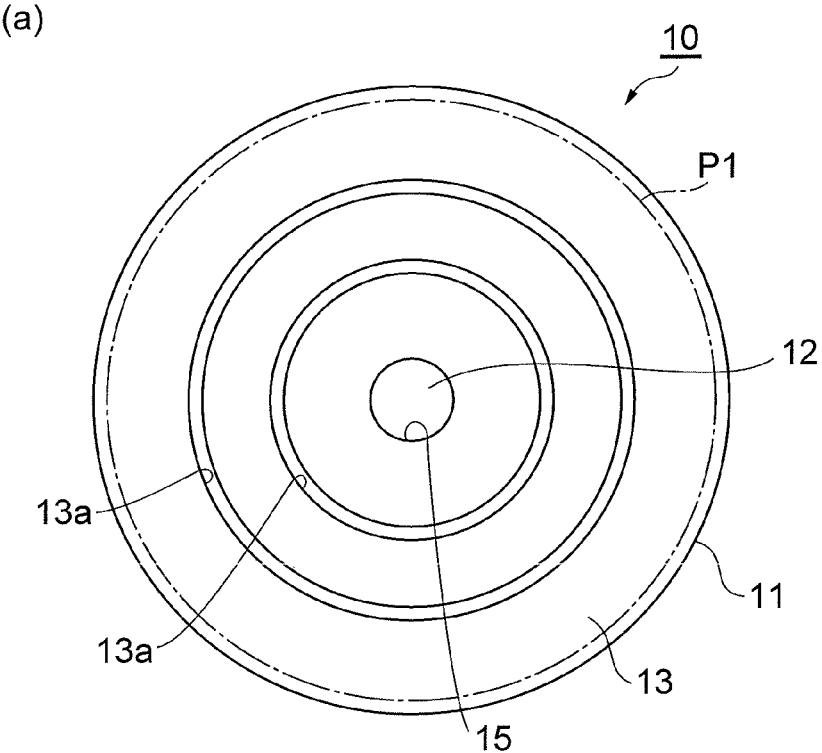
(b)
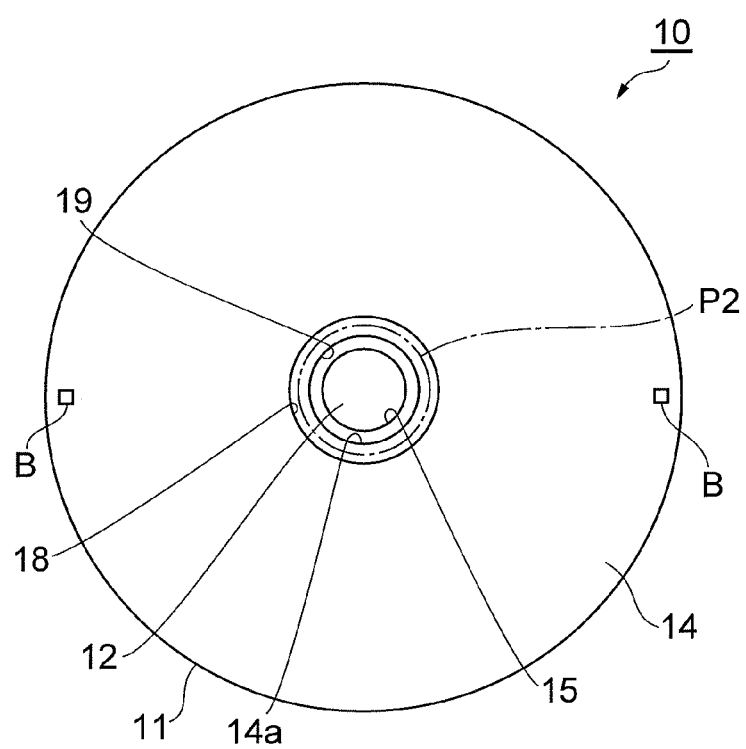

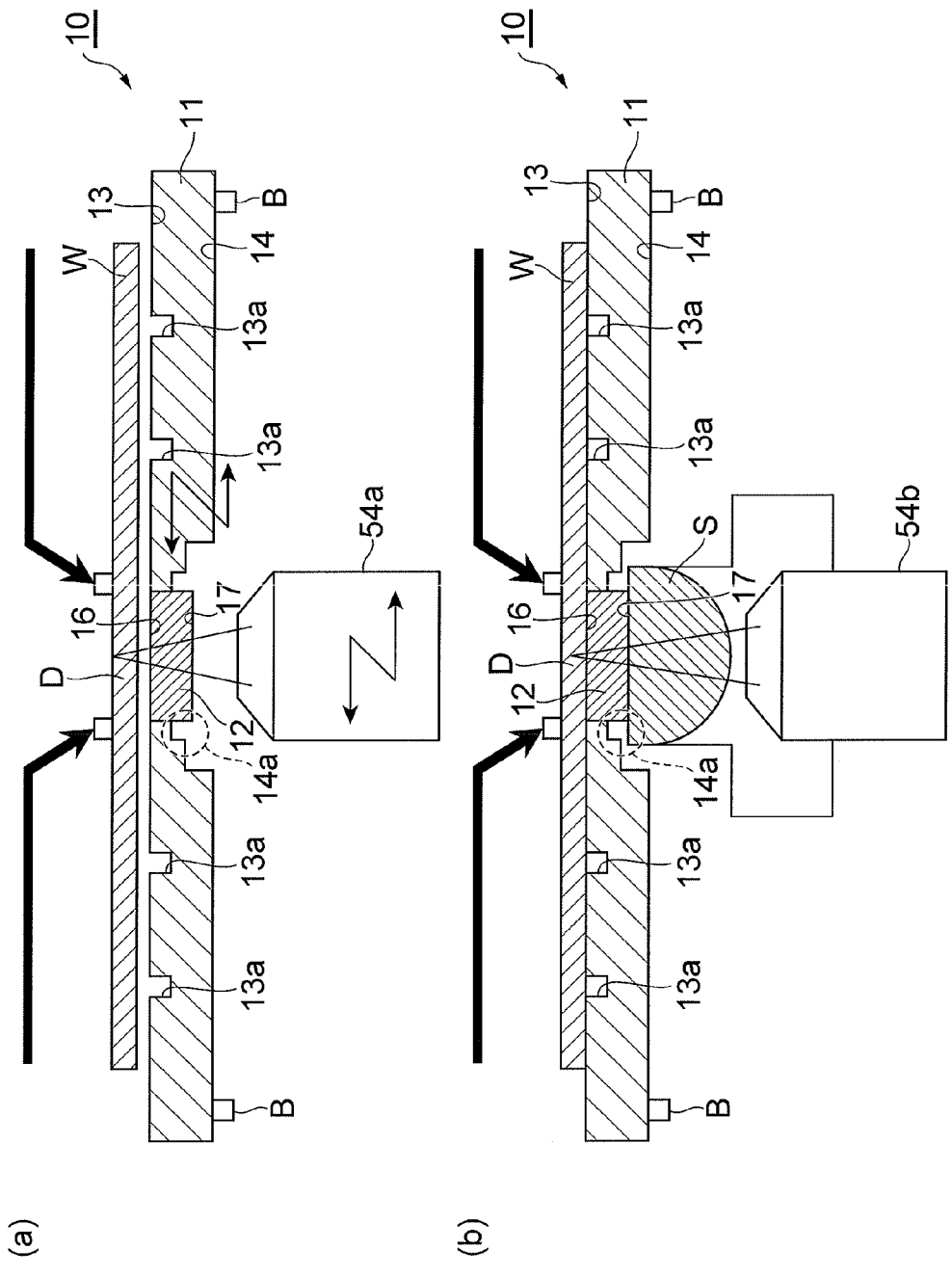

SUCTION APPARATUS, SEMICONDUCTOR DEVICE OBSERVATION DEVICE, AND SEMICONDUCTOR DEVICE OBSERVATION METHOD

TECHNICAL FIELD

The present invention relates to a suction unit, a semiconductor device observation apparatus, and a semiconductor device observation method.

BACKGROUND ART

In recent years, miniaturization of semiconductor devices has been advanced. Therefore, it has been proposed, when observing semiconductor devices to perform failure analysis of the semiconductor devices, to use a solid immersion lens in order to improve resolution (refer to, for example, Patent Document 1). In the failure analysis system described in Patent Document 1, a substantially hemispherical solid immersion lens is formed integrally with an analytical plate to place thereon a semiconductor wafer formed with semiconductor devices.

CITATION LIST

Patent Literature

Patent Document 1: Japanese Patent Application Laid-Open No. 2008-141207

SUMMARY OF INVENTION

Technical Problem

Meanwhile, when failure analysis of a semiconductor device is performed, it is desired to first perform observation of a semiconductor device at a low magnification without using a solid immersion lens to detect a failure site, and then perform observation of the failure site at a high magnification using a solid immersion lens.

However, in the failure analysis system described in Patent Document 1, as mentioned above, the analytical plate to place thereon a semiconductor wafer and the solid immersion lens are integrally formed, so that for fitting and removing the solid immersion lens, it is necessary to fit and remove the analytical plate as a whole. Therefore, it has been difficult in this failure analysis system to change over observation at a low magnification without using a solid immersion lens and observation at a high magnification using a solid immersion lens.

It is therefore an object of the present invention to provide a suction unit, a semiconductor device observation apparatus, and a semiconductor device observation method which allow easily performing changeover between observation at a low magnification and observation at a high magnification of a semiconductor device.

Solution to Problem

An aspect of the present invention relates to a suction unit. This suction unit is a suction unit to be used for a semiconductor device observation apparatus for performing observation of a semiconductor device by use of a solid immersion lens, and is characterized by including a main body portion having a first surface on which a semiconductor wafer formed with the semiconductor device is arranged and a second surface that is a surface opposite to the first surface, and in which a through-hole that penetrates through the first surface and the second surface is formed, and a light transmitting portion having a light incident surface onto which light from the semiconductor device is made incident and a light emitting surface from which light made incident from the light incident surface is emitted, and which is fitted to the through-hole so that the light incident surface is exposed to a side of the first surface and the light emitting surface is exposed to a side of the second surface, and in that in the first surface, a first suction groove for vacuum sucking the semiconductor wafer to fix the semiconductor device to the light incident surface is formed, and in the second surface, a second suction groove for vacuum sucking the solid immersion lens to fix the solid immersion lens to the light emitting surface is formed.

By this suction unit, the semiconductor device is suction fixed to the light incident surface by vacuum suction using the first suction groove, while the solid immersion lens can be suction fixed to the light emitting surface by vacuum suction using the second suction groove. Moreover, by suction fixing the semiconductor device to the light incident surface in the same manner while stopping the vacuum suction using the second suction groove, the suction fixing of the solid immersion lens can also be released. Thus, by this suction unit, the solid immersion lens can be easily fitted and removed with the semiconductor device to serve as an observation object being suction fixed to the light incident surface. Therefore, by this suction unit, observation of the semiconductor device at a low magnification without using the solid immersion lens and observation of the semiconductor device at a high magnification using the solid immersion lens can be easily changed over. In particular, this is effective for observation of a semiconductor device formed in a semiconductor wafer.

In the suction unit according to an aspect of the present invention, a recess portion to arrange the solid immersion lens may be formed in the second surface, the through-hole may be formed in a bottom surface of the recess portion, the light emitting surface may be located so as to project to the second surface side further than the bottom surface of the recess portion, and the second suction groove may be formed along an edge portion of the through-hole on the bottom surface of the recess portion. In this case, the distance between the solid immersion lens and the light emitting surface can be made short, so that evanescent coupling between the solid immersion lens and the light transmitting portion can be reliably realized. Moreover, because the bottom surface of the solid immersion lens and the bottom surface of the recess portion separate from each other (that is, the second suction groove is not closed) when the solid immersion lens is fixed to the light emitting surface by vacuum suction, by stopping the vacuum suction, the suction fixing of the solid immersion lens can be easily released.

Moreover, in the suction unit according to an aspect of the present invention, the light transmitting portion may be made of a material having substantially the same refractive index as that of a material to form a substrate of the semiconductor device. In this case, aberration to be caused by a difference in refractive index can be suppressed.

Moreover, the suction unit according to an aspect of the present invention may further include a cooling means for cooling the main body portion. In this case, overheating of the semiconductor device and the solid immersion lens can be avoided. As a result, a normal operation of the semiconductor device can be realized, and a change in the refractive index of the solid immersion lens can be prevented.

Another aspect of the present invention relates to a semiconductor device observation apparatus. This semiconductor device observation apparatus is a semiconductor device observation apparatus for performing observation of a semiconductor device by use of a solid immersion lens, and is characterized by including the suction unit described above, a light guide optical system for guiding light transmitted through the light transmitting portion, and an imaging means for imaging light guided by the light guide optical system.

Because this semiconductor device observation apparatus includes the suction unit described above, observation of the semiconductor device at a low magnification without using the solid immersion lens and observation of the semiconductor device at a high magnification using the solid immersion lens can be easily changed over. In particular, this is effective for observation of a semiconductor device formed in a semiconductor wafer.

In the semiconductor device observation apparatus according to another aspect of the present invention, the light guide optical system may include a first objective lens having a predetermined magnification, a second objective lens having a magnification higher than the predetermined magnification, and an objective lens switching means for switching the first objective lens and the second objective lens, and to the second objective lens, in a manner movable in a direction along its optical axis, the solid immersion lens may be attached. In this case, the solid immersion lens is made movable, relative to the second objective lens of high power, in its optical axis direction. Therefore, even after the solid immersion lens is suction fixed, the second objective lens can be moved to adjust the focus position.

Moreover, the semiconductor device observation apparatus according to another aspect of the present invention may further include a voltage application means for applying voltage to the semiconductor device.

Still another aspect of the present invention relates to a semiconductor device observation method. This semiconductor device observation method is a semiconductor device observation method for observing a semiconductor device formed in a semiconductor wafer, and is characterized by including a voltage application step of applying voltage to a predetermined site of the semiconductor device arranged on a light incident surface of a light transmitting portion of a suction unit, a detection step of detecting a site to be observed in the semiconductor device by observing light emitted from the semiconductor device and to be transmitted through the light transmitting portion by use of a first objective lens arranged on a side of a light emitting surface opposite to the light incident surface of the light transmitting portion, an alignment step of aligning a second objective lens having a magnification higher than that of the first objective lens and a solid immersion lens attached to the second objective lens, on the light emitting surface side, with the site to be observed detected in the detection step, a suction fixing step of fixing the solid immersion lens to the light emitting surface by vacuum suction, a focus adjusting step of adjusting a focus of the second objective lens by adjusting the position of the second objective lens in an optical axis direction of the second objective lens, and an image acquisition step of acquiring an image of the site to be observed by use of the second objective lens.

In this semiconductor device observation method, observation of the semiconductor device is performed by the first objective lens of low magnification without using the solid immersion lens to detect a site to be observed, and thereafter, the solid immersion lens is suction fixed to the light emitting surface of the suction unit, and observation of the site to be observed of the semiconductor device is performed by the second objective lens of high magnification. Thus, by this semiconductor device observation method, observation of the semiconductor device at a low magnification without using the solid immersion lens and observation of the semiconductor device at a high magnification using the solid immersion lens can be easily changed over. In particular, this is effective for observation of a semiconductor device formed in a semiconductor wafer.

In the semiconductor device observation method according to still another aspect of the present invention, in the voltage application step, voltage may be applied to the semiconductor device with the semiconductor device fixed to the light incident surface by vacuum sucking of the semiconductor wafer, and in the detection step, the site to be observed may be detected by observing light from the semiconductor device while adjusting a positional relationship between the first objective lens and the light transmitting portion.

In this case, voltage is applied to the semiconductor device with the semiconductor device suction fixed to the light incident surface, and the positional relationship between the first objective lens and the light transmitting portion is adjusted while the semiconductor device is observed. Therefore, this semiconductor device observation method can be effectively applied when the width of the light transmitting portion is relatively large to the width of the semiconductor device. Further, in such a case, because it is not necessary to change the positional relationship between the semiconductor device and the light transmitting portion when detecting a site to be observed of the semiconductor device, the site to be observed is easily identified.

Moreover, the semiconductor device observation method according to still another aspect of the present invention may further include, between the detection step and the alignment step, a suction unit moving step of retaining the semiconductor wafer to float up from the suction unit by blowout of air from the suction unit, moving the suction unit relative to the semiconductor device to align the light transmitting portion with the site to be observed detected in the detection step, and fixing the semiconductor device to the light incident surface by vacuum sucking the semiconductor wafer, and in the alignment step, the second objective lens and the solid immersion lens may be aligned with the site to be observed with which the light transmitting portion is aligned.

In this case, the semiconductor wafer is retained to float up from the suction unit, and the light transmitting portion is moved relative to the semiconductor device to align the light transmitting portion with the site to be observed. Accordingly, this semiconductor device observation method can be effectively applied when the width of the light transmitting portion is relatively small to the width of the semiconductor device. Further, in such a case, because the contact area between the light incident surface and the semiconductor device and the contact area between the light emitting surface and the solid immersion lens are relatively small, the suction efficiency of the semiconductor device and the solid immersion lens is high. Accordingly, evanescent coupling can be reliably realized at an interface between the semiconductor device and the light incident surface and an interface between the light emitting surface and the solid immersion lens.

Moreover, in the semiconductor device observation method according to still another aspect of the present invention, in the alignment step, by retaining the semiconductor wafer to float up from the suction unit by blowout of air from the suction unit, and integrally moving the suction unit, the second objective lens, and the solid immersion lens, the suction unit, the second objective lens, and the solid immersion lens may be aligned with the site to be observed. In this case, because the suction unit, the second objective lens, and the solid immersion lens are integrally moved and aligned with the site to be observed, a plurality of sites to be observed can be easily observed.

Further, in the semiconductor device observation method according to still another aspect of the present invention, in the suction fixing step, after bringing the solid immersion lens into contact with the light emitting surface by moving the solid immersion lens in the optical axis direction of the second objective lens, the solid immersion lens may be fixed to the light emitting surface by vacuum suction. In this case, because the solid immersion lens is suction fixed to the light emitting surface after being brought into contact therewith, misalignment of the solid immersion lens can be prevented.

Advantageous Effects of Invention

According to the present invention, a suction unit, a semiconductor device observation apparatus, and a semiconductor device observation method which allow easily performing changeover between observation at a low magnification and observation at a high magnification of a semiconductor device can be provided.

BRIEF DESCRIPTION OF DRAWINGS

FIG. 2 are plan views of the suction unit shown in FIG. 1.

FIG. 14 are views schematically showing some steps of the second embodiment of a semiconductor device observation method according to the present invention.

DESCRIPTION OF EMBODIMENTS

Figure 1:
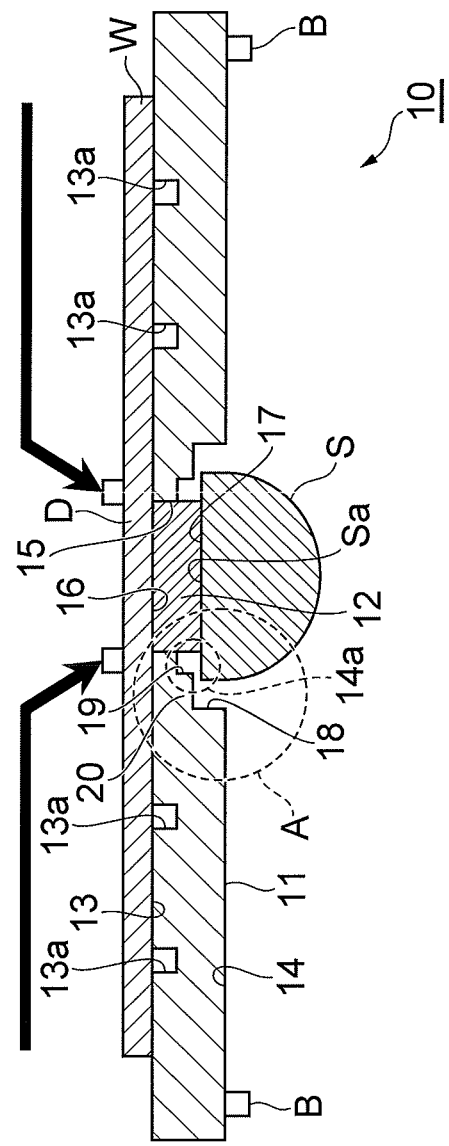
FIG. 1 is a sectional view showing a configuration of an embodiment of a suction unit according to the present invention.

Hereinafter, embodiments of a suction unit, a semiconductor device observation apparatus including the same, and a semiconductor device observation method according to the present invention will be described in detail with reference to the drawings. In the description of the drawings, the same or corresponding parts are denoted by the same reference signs, and overlapping description will be omitted. Also, the dimensional ratios of parts in the drawings are not always coincident with actual ratios.

[Embodiment of Suction Unit]

Figure 3:
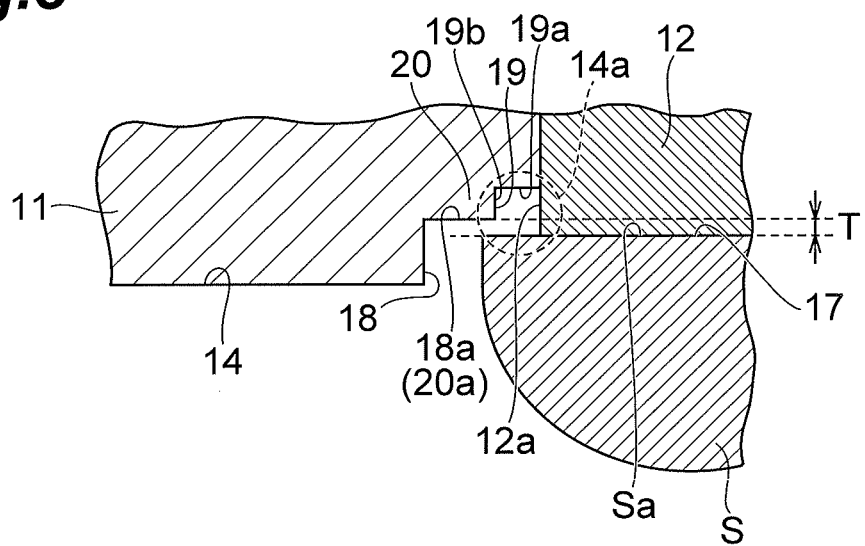
FIG. 3 is a partially enlarged view of the suction unit shown in FIG. 1.

First, an embodiment of a suction unit according to the present invention will be described. FIG. 1 is a sectional view showing a configuration of an embodiment of a suction unit according to the present invention, FIG. 2(a) is a plan view observed from the side of a first surface of the suction unit shown in FIG. 1, and FIG. 2(b) is a plan view observed from the side of a second surface of the suction unit shown in FIG. 1. Moreover, FIG. 3 is an enlarged view of the region A shown in FIG. 1. In FIGS. 2 and 3, a semiconductor wafer is omitted. As shown in FIGS. 1 to 3, the suction unit 10 includes a main body portion 11 and a light transmitting portion 12. The suction unit 10 can be used for, for example, a semiconductor device observation apparatus for performing observation of a semiconductor device by use of a solid immersion lens (SIL: Solid Immersion Lens).

The main body portion 11 has a first surface 13 on which a semiconductor wafer W formed with a semiconductor device D is arranged. The semiconductor wafer W is arranged, on the first surface 13, in an arrangement position P1 shown by the alternate long and short dashed line in FIG. 2(a). Moreover, the main body portion 11 has a second surface 14 on the opposite side to the first surface 13. Further, in the main body portion 11, a through-hole 15 that penetrates through the first surface 13 and the second surface 14 is formed. The main body portion 11 shows a disk shape, and the through-hole 15 is formed in a circular cylindrical shape at is inner wall of in a substantially central portion of the main body portion 11. The shape of the main body portion 11 is not limited to a disk shape. Also, the through-hole 15 is not limited to one the inner wall of which is in a circular cylindrical shape.

The light transmitting portion 12 is fitted to the through-hole 15, and fixed by an adhesive or the like. Moreover, the light transmitting portion 12 has a light incident surface 16 onto which light from the semiconductor device D arranged on the first surface 13 is made incident and a light emitting surface 17 from which light made incident from the light incident surface 16 is emitted. The light incident surface 16 and the light emitting surface 17 are opposed to each other. Therefore, the light transmitting portion 12 shows a columnar shape defined using the light incident surface 16 and the light emitting surface 17 as both end surfaces. The shape of the light transmitting portion 12 is not limited to a columnar shape.

The light incident surface 16 is exposed to the side of the first surface 13. Moreover, the light incident surface 16 is flush with the first surface 13. Therefore, if a semiconductor wafer W is arranged on the first surface 13, a predetermined semiconductor device D of the semiconductor wafer W is then arranged on the light incident surface 16. The light emitting surface 17 is exposed to the side of the second surface 14. Therefore, light from the semiconductor device D is transmitted through the suction unit 10 via the light transmitting portion 12.

Here, in the first surface 13 of the main body portion 11, plurality of (here, two) first suction grooves 13a for vacuum sucking the semiconductor wafer W arranged on the first surface 13 to suction fix the semiconductor device D to the light incident surface 16 are formed. These first suction grooves 13a are formed in ring shapes that are concentric with an edge portion of the first surface 13. Each of the first suction grooves 13a communicates with at least one of the plurality of suction ports B provided on the second surface 14 in the vicinity of an outer edge of the main body portion 11, and the interior thereof is vacuumed by a vacuum pump or the like connected to that suction port B. In this case, there may be a configuration to allow selecting a first suction groove(s) 13a to be used for vacuum suction according to the shape and size of the semiconductor wafer W. Moreover, the shapes of the first suction grooves 13a are not limited to ring shapes.

Moreover, in the second surface 14 of the main body portion 11, a first recess portion 18 to arrange a solid immersion lens S is formed. The solid immersion lens S is arranged in an arrangement position P2 shown by the alternate long and short dashed line in FIG. 2(b). The first recess portion 18 is formed in a columnar shape concentric with an edge portion of the second surface 14. In a bottom surface 18a of the first recess portion 18, a second recess portion 19 similarly showing a columnar shape concentric with the edge portion of the second surface 14 is formed. Therefore, in the main body portion 11, a step portion 20 is formed by the bottom surface 18a of the first recess portion 18, a bottom surface 19a of the second recess portion 19, and a side surface 19b of the second recess portion 19. The through-hole 15 described above is formed in the bottom surface 19a of the second recess portion 19. In addition, the light transmitting portion 12 fitted to the through-hole 15 projects from the bottom surface 19a of the second recess portion 19 toward the second surface 14.

Here, in the second surface 14 of the main body portion 11, a second suction groove 14a for fixing, in close contact with the light emitting surface 17, a bottom surface Sa that is a planar portion of the solid immersion lens S by vacuum sucking the solid immersion lens S is formed. The light transmitting portion 12 is arranged inside of the second suction groove 14a. More specifically, the second suction groove 14a is formed in an annular shape along an edge portion of the through-hole 15 by a side surface 12a of the light transmitting portion 12 and the bottom surface 19a and the side surface 19b that are inner surfaces of the second recess portion 19. Such a second suction groove 14a communicates with a suction port B different from the suction port B with which the first suction groove 13a is communicated, and the interior thereof is vacuumed by a vacuum pump or the like connected to the suction port B. Here, the light transmitting portion 12 projects from the bottom surface 18a of the first recess portion 18 toward the second surface 14. When described in detail, the light emitting surface 17 is located on the second surface 14 side further by a distance T than the bottom surface 18a of the first recess portion 18, that is, an upper surface 20a of the step portion 20. Therefore, when the solid immersion lens S is arranged on the light emitting surface 17, the bottom surface Sa of the solid immersion lens S and the bottom surface 18a of the first recess portion 18 separate from each other (that is, the second suction groove 14a is not closed). Accordingly, as a result of vacuuming the interior of the second suction groove 14a, a difference in atmospheric pressure occurs between the interior and exterior of the second suction groove 14a, and the solid immersion lens S is suction fixed to the light emitting surface 17. In other words, the "vacuum suction" referred to here includes suction by vacuuming of such an unclosed groove in addition to suction by vacuuming of a groove structured to be airtight.

The main body portion 11 can be made of, for example, Cu that is excellent in thermal conductivity and easy to be processed. In this case, heat generated by the semiconductor wafer arranged on the main body portion 11 can be absorbed (dissipated). Moreover, the light transmitting portion 12 can be provided as a portion made of a material (such as, for example, Si, GaP, and GaAs when the substrate of the semiconductor device D is Si) having substantially the same refractive index as that of a material to form the substrate of the semiconductor device D. Here, having substantially the same refractive index means that a difference between each others' refractive indices is within, for example, 5%, but this may be appropriately changed depending on a numerical aperture NA to be achieved. Thus, by forming the light transmitting portion 12 made of a material having substantially the same refractive index as that of the material of the substrate of the semiconductor device D, the numerical aperture NA can be increased.

Particularly, when the substrate of the semiconductor device D is Si, it is preferable that the light transmitting portion 12 is also made of Si, and when the substrate of the semiconductor device D is GaAs, it is preferable that the light transmitting portion 12 is also made of GaAs. In other words, it is preferable to form the light transmitting portion 12 made of the same material as the material to form the substrate of the semiconductor device D.

When the light transmitting portion 12 and the solid immersion lens S are both GaP having a refractive index of 3.2 and the thickness of the substrate of the semiconductor device D made of Si is 100 μm, the numerical aperture NA of the whole is 2.3. On the other hand, when the light transmitting portion 12 and the solid immersion lens S are both GaAs having a refractive index of 3.45 and the thickness of the substrate of the semiconductor device D made of Si is 800 μm, the numerical aperture NA of the whole is 2.45.

As described above, by the suction unit 10 according to the present embodiment, the semiconductor device D is suction fixed to the light incident surface 16 by vacuum suction using the first suction grooves 13a, while the solid immersion lens S can be suction fixed to the light emitting surface 17 by vacuum suction using the second suction groove 14a. Moreover, by suction fixing the semiconductor device D to the light incident surface 16 in the same manner while stopping the vacuum suction using the second suction groove 14a, the suction fixing of the solid immersion lens S can be released to remove the solid immersion lens S from the light emitting surface 17. Thus, by the suction unit 10, the solid immersion lens S can be easily fitted and removed with the semiconductor device D to serve as an observation object being suction fixed to the light incident surface 16. Therefore, by the suction unit 10, observation of the semiconductor device D at a low magnification without using the solid immersion lens S and observation of the semiconductor device D at a high magnification using the solid immersion lens S can be easily changed over.

Meanwhile, for realizing evanescent coupling between the solid immersion lens S and the light transmitting portion 12, it is necessary to bring the bottom surface Sa of the solid immersion lens S and the light emitting surface 17 into close contact with each other so that the distance between the bottom surface Sa of the solid immersion lens S and the light emitting surface 17 becomes one tenth or less than the wavelength of observation light. In the suction unit 10 according to the present embodiment, the light emitting surface 17 is located so as to project to the second surface 14 side further than the bottom surface 18a of the first recess portion 18 (that is, the upper surface 20a of the step portion 20). Accordingly, when suction fixing the solid immersion lens S to the light emitting surface 17 by use of the second suction groove 14a, contact of an edge portion of the second suction groove 14a with the bottom surface Sa of the solid immersion lens S can be avoided. As a result, the bottom surface Sa of the solid immersion lens S and the light emitting surface 17 can be sufficiently brought into close contact with each other, and evanescent coupling can be reliably realized. Moreover, because the bottom surface Sa of the solid immersion lens S and the bottom surface 18a of the first recess portion 18 are separate from each other (that is, the second suction groove 14a is not closed), by stopping vacuum suction using the second suction groove 14a, suction fixing of the solid immersion lens S can be easily released.

Figure 4:
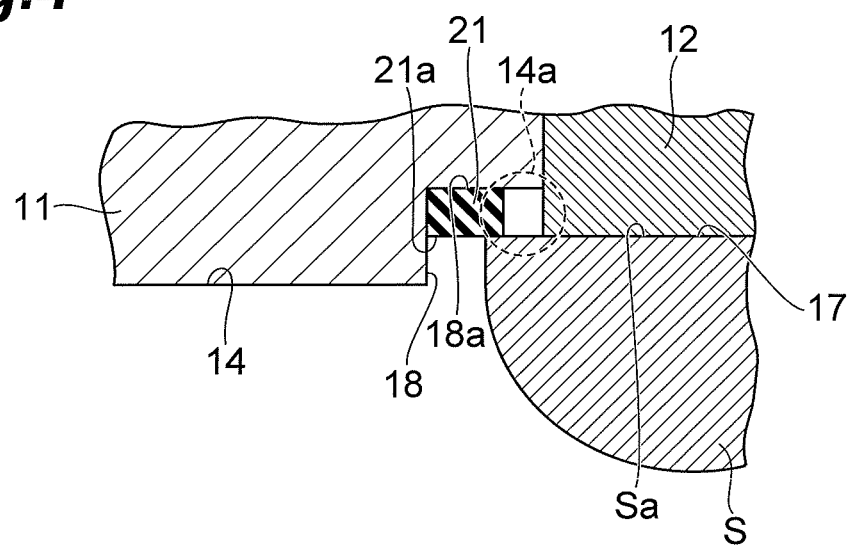
FIG. 4 is a partially enlarged view showing a modification of the suction unit shown in FIG. 1.

In the suction unit 10, in place of forming the step portion 20, as shown in FIG. 4, an annular sealing member 21 made of an elastic material (such as, for example, elastic) may be arranged on the bottom surface 18a of the first recess portion 18. At this time, an upper surface 21a of the sealing member 21 is located on the second surface 14 side further than the light emitting surface 17. In this case, the airtightness of the second suction groove 14a is improved (that is, the second suction groove 14a is closed) when the solid immersion lens S is arranged on the light emitting surface 17, the solid immersion lens S can be efficiently sucked. Moreover, when vacuum suction using the second suction groove 14a is stopped, the bottom surface Sa of the solid immersion lens S comes off toward the second surface 14 due to elasticity of the sealing member 21, so that suction fixing of the solid immersion lens S can be easily released.

Moreover, the suction unit 10 can further include a cooling means for cooling the main body portion 11. In this case, overheating of the semiconductor device D and the solid immersion lens S can be avoided. As a result, a normal operation of the semiconductor device D can be realized, and a change in the refractive index of the solid immersion lens S can be prevented.

[Embodiment of Semiconductor Device Observation Apparatus]

Figure 5:
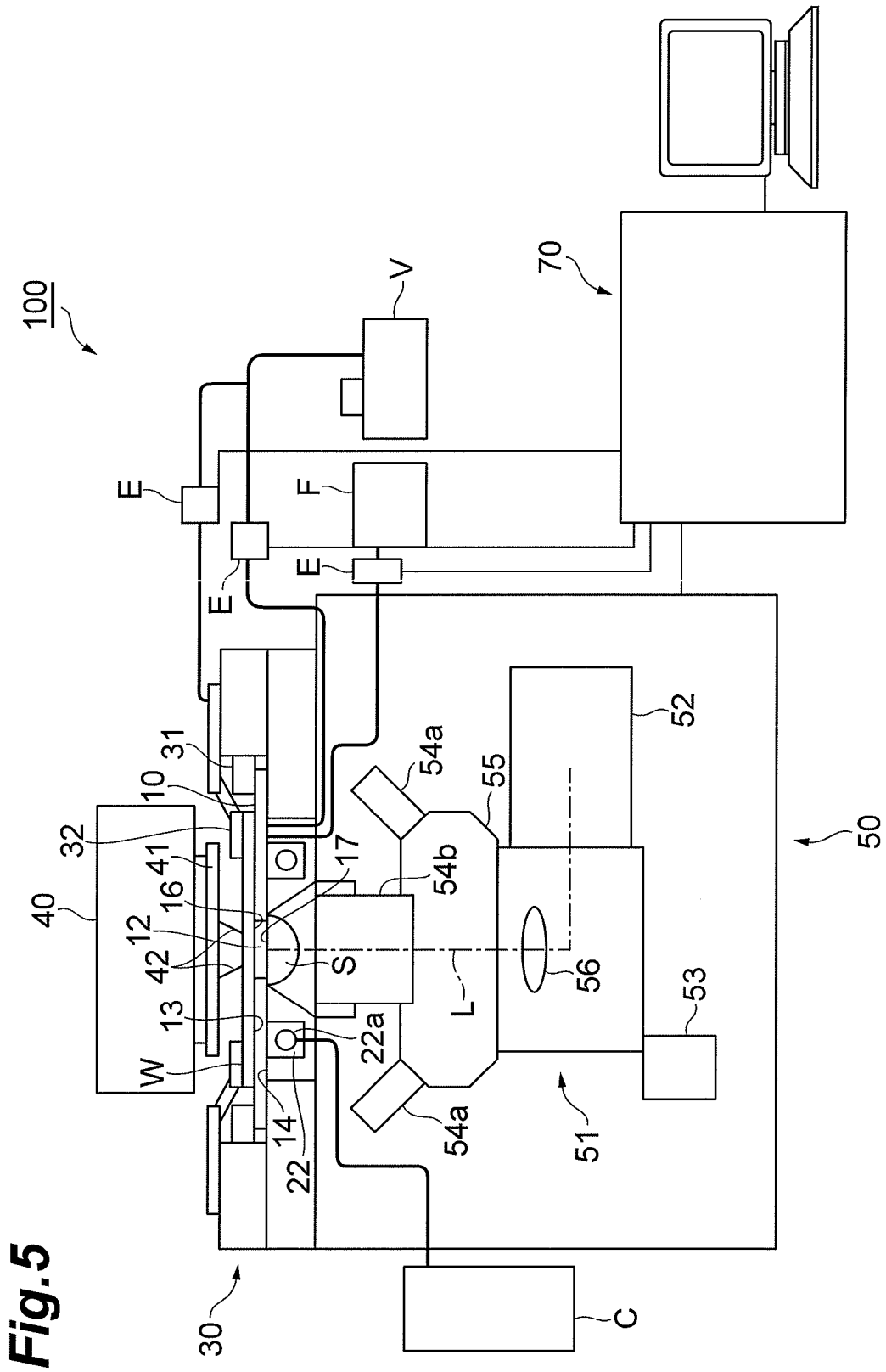
FIG. 5 is a view schematically showing a configuration of an embodiment of a semiconductor device observation apparatus according to the present invention.

Next, an embodiment of a semiconductor device observation apparatus according to the present invention will be described. FIG. 5 is a view schematically showing a configuration of an embodiment of a semiconductor device observation apparatus according to the present invention. As shown in FIG. 5, the semiconductor device observation apparatus 100 includes a suction device section 30, a tester (voltage application means) 40, an optical device section 50, and a control section 70. The semiconductor device observation apparatus 100 can be used in such a case, for example, where a semiconductor device is observed by use of a solid immersion lens for failure analysis of the semiconductor device.

The suction device section 30 has the suction unit 10 mentioned above. In the suction unit 10, a semiconductor wafer W formed with a semiconductor device D that is an observation object of the semiconductor device observation apparatus 100 is arranged. The suction device section 30 further has a suction unit drive mechanism 31 for driving the suction unit 10 in an X-Y direction (extending direction of the light incident surface 16 and the light emitting surface 17), and a wafer suction fixing portion 32 for suction fixing the semiconductor wafer W arranged on the first surface 13. The wafer suction fixing portion 32 can be used for, for example, positioning of the semiconductor wafer W with respect to the suction unit 10.

Moreover, the suction unit 10 further has a water cooling jacket (cooling means) 22 for cooling the main body portion 11. The water cooling jacket 22 is provided on the second surface 14. The water cooling jacket 22 has a coolant channel 22a formed in an annular shape, and cools the main body portion 11 by causing a coolant supplied from a coolant chiller C to circulate through the coolant channel 22a.

Moreover, to the first suction grooves 13a and the second suction groove 14a, a vacuum pump V is connected via the suction ports B and valves E. Moreover, also to the wafer suction fixing portion 32, the vacuum pump V is similarly connected via a valve E. Further, to the first suction grooves 13a, an air compressor F is connected via a valve E. These valves E can be provided as, for example, solenoid valves.

The tester 40 applies voltage to the semiconductor device D of the semiconductor wafer W arranged on the first surface 13. More specifically, the tester 40 generates an electrical signal necessary for observation of the semiconductor device D, and supplies the generated electrical signal to the semiconductor device D via a probe card 41 and a probe pin 42.

The optical device unit 50 has a light guide optical system 51 for guiding light transmitted through the light transmitting portion 12, a detector (imaging means) 52 for detecting and imaging light guided by the light guide optical system 51, and an XYZ stage 53 for driving the light guide optical system 51 in the X-Y direction and a Z direction (direction along an optical axis L of the light guide optical system 51) perpendicular thereto.

The light guide optical system 51 includes a low-power objective lens (first objective lens) 54a and a high-power objective lens (second objective lens) 54b onto which light transmitted through the light transmitting portion 12 is made incident, a lens turret (objective lens switching means) 55 for switching the low-power objective lens 54a and the high-power objective lens 54b, and an imaging lens 56 for focusing light from the low-power objective lens 54a and the high-power objective lens 54b.

The high-power objective lens 54b has a magnification higher than that of the low-power objective lens 54a. Moreover, to the high-power objective lens 54b, in a manner movable along at least its optical axis L, the solid immersion lens S is attached. A state where the solid immersion lens S is attached to the high-power objective lens 54b is shown in FIG. 6.

Figure 6:
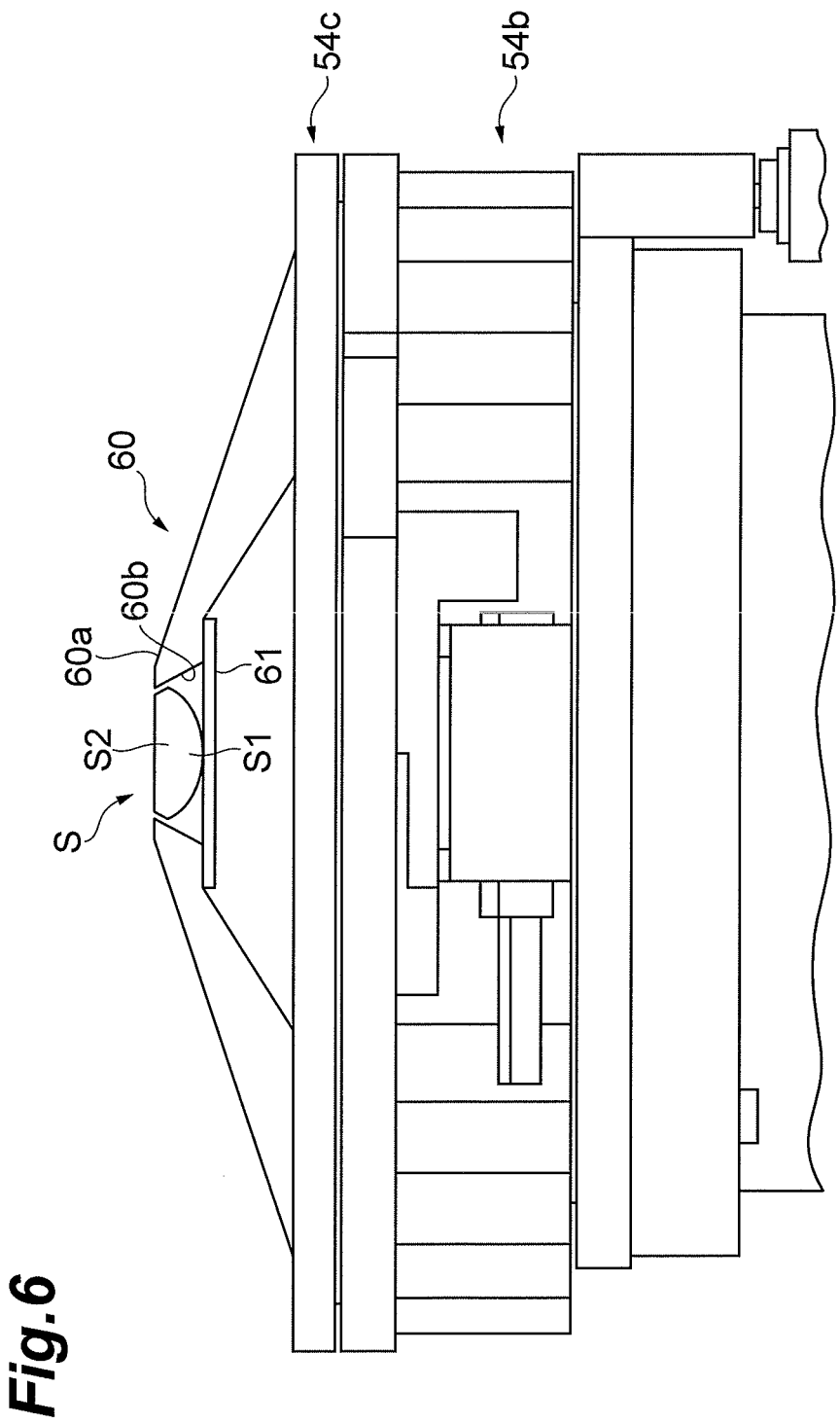
FIG. 6 is a partially enlarged view of the high-power objective lens shown in FIG. 5.

As shown in FIG. 6, the solid immersion lens S here consists of a substantially hemispheric first part S1 and a second part S2 having a tapered shape. At a tip portion 54c of the high-power objective lens 54b, a lens holder 60 for holding such a solid immersion lens S is attached. An inner surface 60b of a tip portion 60a of the lens holder 60 is inclined in line with the tapered shape of the second part S2 of the solid immersion lens S. Accordingly, the solid immersion lens S held by the lens holder 60 is held in a state without being fixed to the lens holder 60 and with its bottom surface Sa made to project from the tip portion 60a of the lens holder 60, and is movable substantially along the optical axis L of the high-power objective lens 54b.

Further, in the lens holder 60, a lens cover 61 that restricts movement of the solid immersion lens S in the direction toward the high-power objective lens 54b is provided. Therefore, the solid immersion lens S is held between the inner surface 60b of the tip portion 60a of the lens holder 60 and the lens cover 61.

Figure 7:
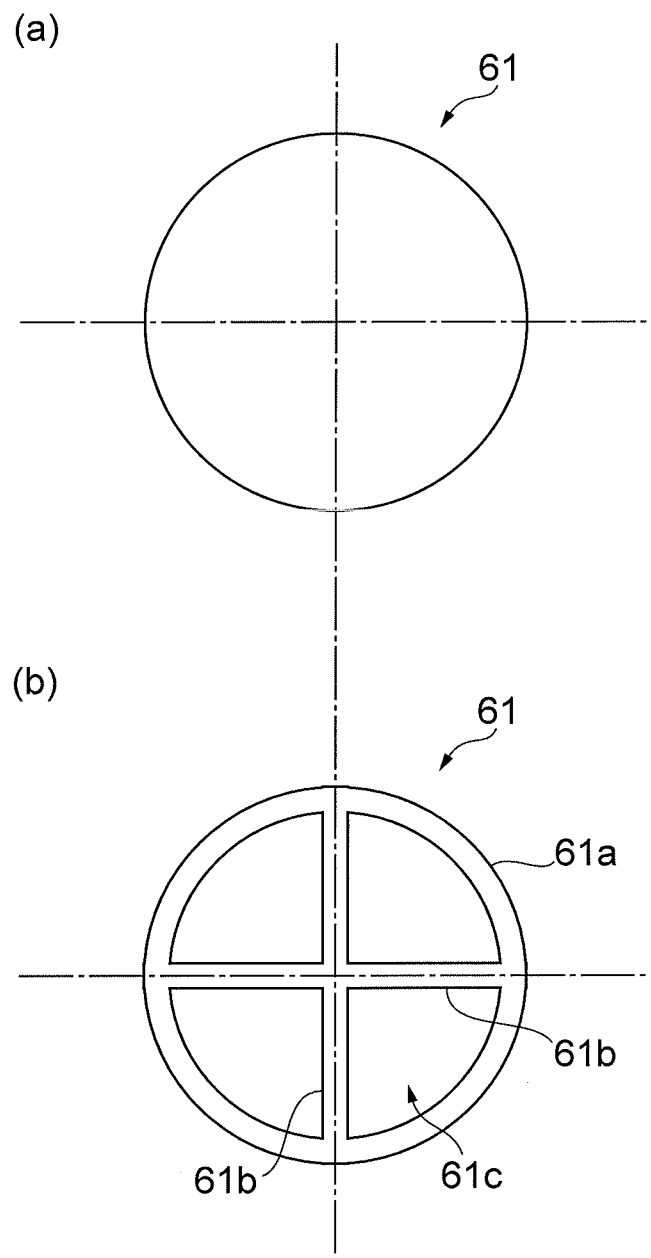
FIG. 7 are plan views showing configurations of the lens cover shown in FIG. 6.

The lens cover 61, when made of a material that transmits observation light, may be provided as, for example, a disk-shaped one as shown in FIG. 7(a). Moreover, the lens cover 61, when made of a material that does not transmit observation light, may be provided in, for example, as shown in FIG. 7(b), a shape where light transmitting openings 61c are provided by a ring-shaped edge portion 61a and support portions 61b bridged on the edge portion 61a.

Figure 8:
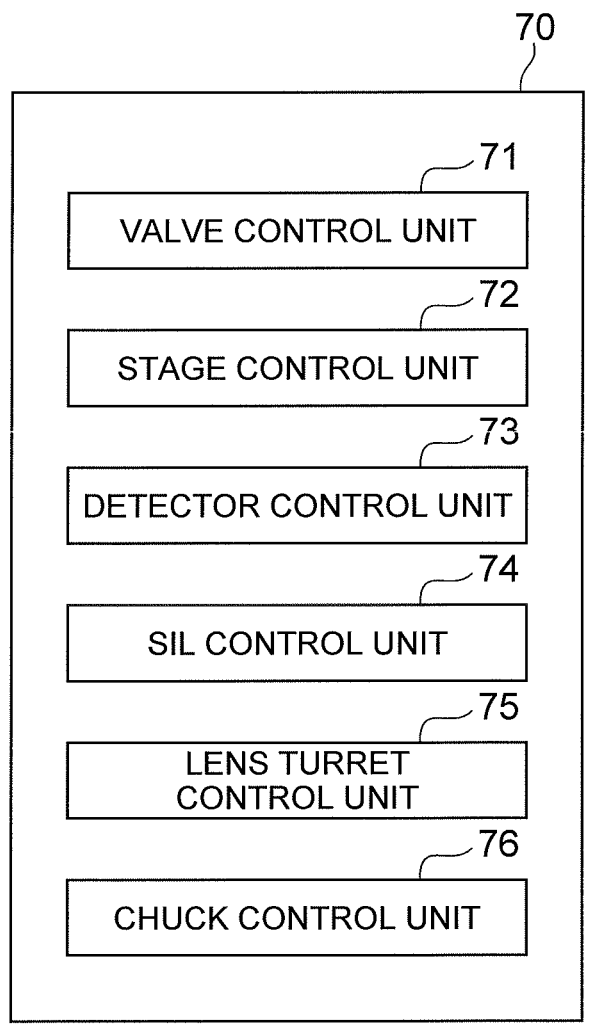
FIG. 8 is a block diagram showing a functional configuration of the control section shown in FIG. 5.

The control section 70 is an electronic control unit for controlling the suction device section 30, the optical device section 50, and the valves E. Such a control section 70 has, functionally, as shown in FIG. 8, a valve control unit 71, a stage control unit 72, a detector control unit 73, an SIL control unit 74, a lens turret control unit 75, and a chuck control unit 76.

The valve control unit 71 controls opening/closing of the valves E. More specifically, the valve control unit 71, when suction fixing the semiconductor wafer W to the first surface 13, opens the valve E arranged between the first suction grooves 13a and the vacuum pump V to vacuum the interior of the first suction grooves 13a, and closes the valve E when releasing the suction fixing of the semiconductor wafer W. Moreover, the valve control unit 71, when suction fixing the solid immersion lens S to the light emitting surface 17, opens the valve E arranged between the second suction groove 14a and the vacuum pump to vacuum the interior of the second suction groove 14a, and closes the valve E when releasing the suction fixing of the solid immersion lens S.

Moreover, the valve control unit 71, when suction fixing the semiconductor wafer W by use of the wafer suction fixing portion 32, opens the valve E arranged between the wafer suction fixing portion 32 and the vacuum pump V, and closes the valve E when releasing the suction fixing. Further, the valve control unit 71, when making the semiconductor wafer W float up from the suction unit 10, opens the valve E between the first suction grooves 13a and the air compressor F to cause blowout of compressed air from the first suction grooves 13a, and closes the valve E when stopping the float-up of the semiconductor wafer W.

The stage control unit 72 controls the XYZ stage 53 to move the light guide optical system 51 in the X-Y-Z directions. The chuck control unit 76 controls the suction unit drive mechanism 31 to move the suction unit 10 in the X-Y direction.

The detector control unit 73 controls the detector 52. More specifically, the detector control unit 73 performs control of a camera or a laser scanning imaging device serving as the detector 52. Examples of the camera that can be mentioned here include a CCD camera, an InGaAs camera, an MCT camera, and a CMOS camera. Moreover, in the detector control unit 73, the gain and offset or the accumulation time etc., can be controlled according to the light amount to be detected by the detector 52.

The SIL control unit 74 performs control of the operation of the solid immersion lens S attached to the high-power objective lens 54b. More specifically, the SIL control unit 74, when pressing the solid immersion lens S against the light emitting surface 17 to cause vacuum suction to the light emitting surface 17, limits the moving amount of the solid immersion lens S so as not to damage the solid immersion lens S, or allows starting vacuum suction of the solid immersion lens S by control of the valve control unit 71 upon sensing that the solid immersion lens S has contacted the light emitting surface 17.

The lens turret control unit 75, by rotating the lens turret 55, switches the low-power objective lens 54a and the high-power objective lens 54b to select a desired magnification. The lens turret control unit 75 enables selecting a desired magnification by storing in advance where in the lens turret 55 what magnification of objective lens is provided. Moreover, the lens turret control unit 75, by limiting the rotating direction of the lens turret 55 to a fixed direction, prevents degradation in position accuracy due to the effect of backlash.

As described above, because the semiconductor device observation apparatus 100 according to the present embodiment includes the suction unit 10, observation of the semiconductor device D at a low magnification without using the solid immersion lens S (that is, observation by the low-power objective lens 54a) and observation of the semiconductor device D at a high magnification using the solid immersion lens S (that is, observation by the high-power objective lens 54b) can be easily changed over under the control of the control section 70.

Figure 9:
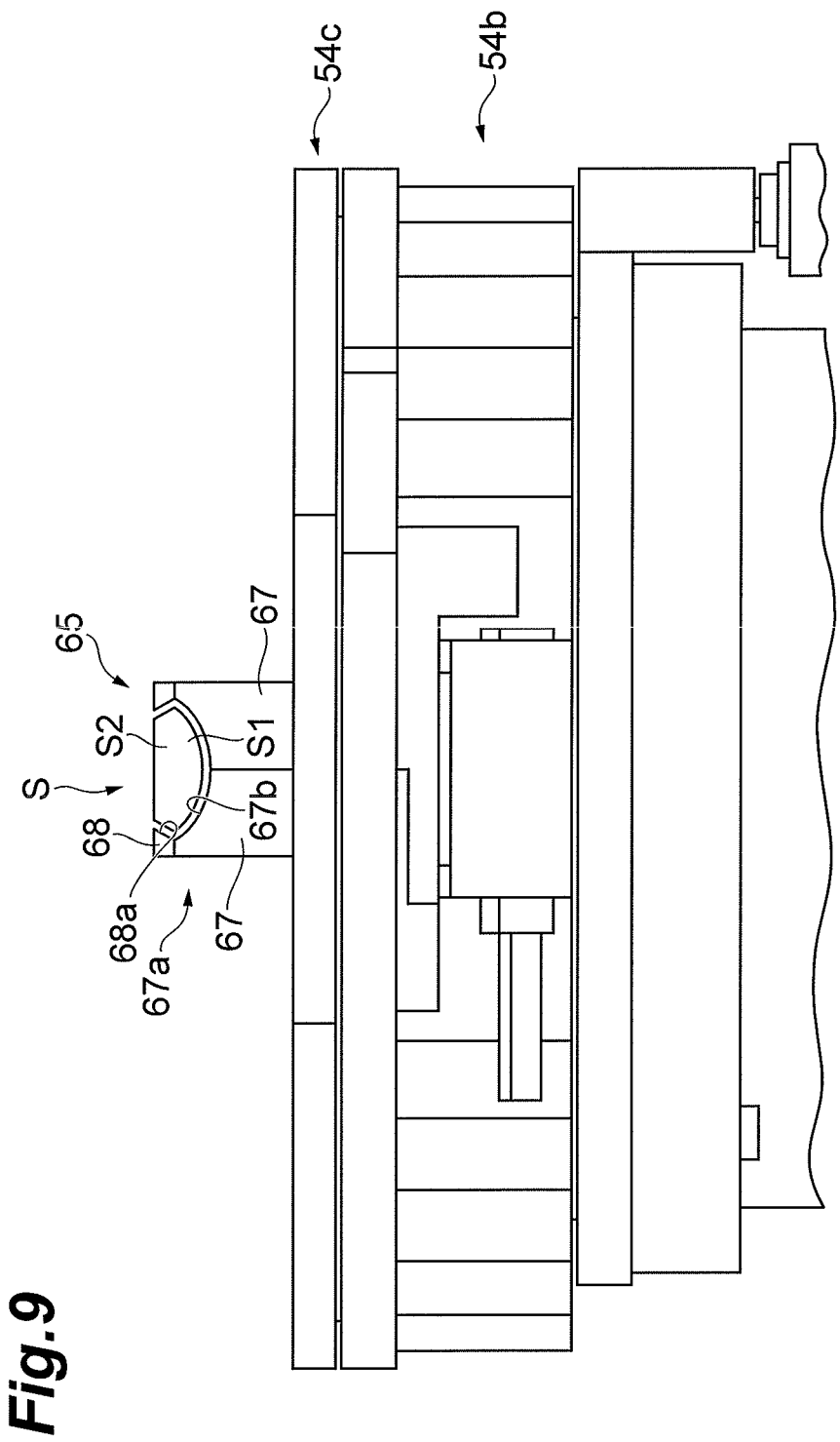
FIG. 9 is a partially enlarged view showing a modification of the high-power objective lens shown in FIG. 5.

The configuration for movably attaching the solid immersion lens S to the high-power objective lens 54b is not limited to the lens holder 60. When the solid immersion lens S is attached to the high-power objective lens 54b, for example, the configuration shown in FIG. 9 can be adopted. In this case, at the tip portion 54c of the high-power objective lens 54b, a lens holder 65 is attached in place of the lens holder 60. The lens holder 65 has a plurality of (for example, three) holding pieces 67.

In the holding piece 67, at its tip portion 67a, a lens receiving surface 67b having substantially the same curvature as that of the first part S1 of the solid immersion lens S is formed, and the solid immersion lens S is arranged on the lens receiving surface 67b. Moreover, at the tip portion 67a of the holding piece 67, a locking piece 68 for locking the solid immersion lens S arranged on the lens receiving surface 67b is disposed. The locking piece 68 is inclined at its inner surface 68a in line with the tapered shape of the second part S2 of the solid immersion lens S. Accordingly, the solid immersion lens S, when having contacted the light emitting surface 17 of the light transmitting portion 12, rotates (turns) in a manner so that its bottom surface Sa follows the light emitting surface 17, while moving so that, by the holding piece 67, a center axis of the solid immersion lens S is held on a radial axis of the holding piece 67. Moreover, the high-power objective lens 54b is movable along the optical axis L, and when performing focus position alignment with an observation position of the semiconductor device D, the relative position of the high-power objective lens 54b to the semiconductor device D is changed for adjustment.

Figure 10:
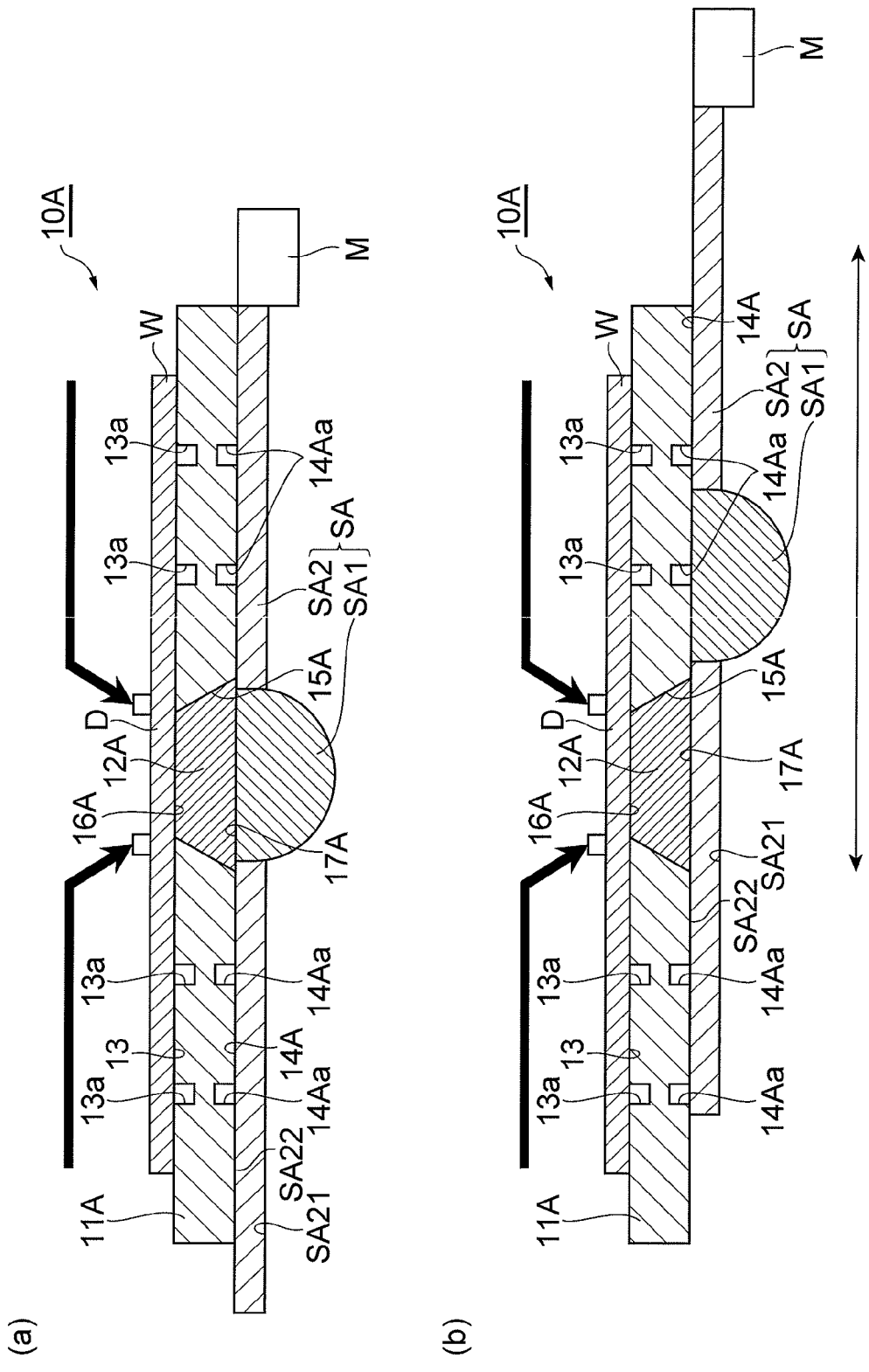
FIG. 10 are sectional views showing a configuration of another embodiment of a suction unit according to the present invention.

Here, FIG. 10 are sectional views showing a configuration of another embodiment of a suction unit according to the present invention. The semiconductor device observation apparatus 100 according to the present embodiment can include the suction unit 10A shown in FIG. 10 in place of the suction unit 10 mentioned above. The suction unit 10A includes a main body portion 11A and a light transmitting portion 12A. The main body portion 11A can be made of the same material (for example, Cu) as that of the main body portion 11 of the suction unit 10. The light transmitting portion 12A can be made of the same material (such as, for example, Si, GaP, GaAs) as that of the light transmitting portion 12 of the suction unit 10.

Similar to the main body portion 11 of the suction unit 10, the main body portion 11A has a first surface 13 on which a semiconductor wafer W formed with a semiconductor device D is arranged. The main body portion 11A has a second surface 14A on the opposite side to the first surface 13. In the main body portion 11A, a through-hole 15A that penetrates through the first surface 13 and the second surface 14A is formed. The main body portion 11A shows a disk shape, and the through-hole 15A is arranged in a substantially central portion of the main body portion 11A. The through-hole 15A exhibits a truncated conical shape that is increased in diameter in the direction from the first surface 13 toward the second surface 14A.

The light transmitting portion 12A is fixed, fitted to the through-hole 15A. The light transmitting portion 12A has a light incident surface 16A onto which light from the semiconductor device D arranged on the first surface 13 is made incident and a light emitting surface 17A from which light made incident from the light incident surface 16A is emitted. The light incident surface 16A and the light emitting surface 17A are opposed to each other. Therefore, the light transmitting portion 12A exhibits a truncated conical shape defined using the light incident surface 16A and the light emitting surface 17A as both end surfaces.

The light incident surface 16A is exposed to the side of the first surface 13. Moreover, the light incident surface 16A is flush with the first surface 13. Therefore, if a semiconductor wafer W is arranged on the first surface 13, a predetermined semiconductor device D of the semiconductor wafer W is then arranged on the light incident surface 16A. The light emitting surface 17A is exposed to the side of the second surface 14A. Therefore, light from the semiconductor device D is transmitted through the suction unit 10A via the light transmitting portion 12A. The light emitting surface 17A is flush with the second surface 14A.

When the suction unit 10A is used, a solid immersion lens SA shown in FIG. 10 can be used in place of the solid immersion lens S. The solid immersion lens SA consists of a hemispherical main body portion SA1 and a planar flange portion SA2. The flange portion SA2 is fixed to the main body portion SA1 at a side base portion of the main body portion SA1, and made movable integrally with the main body portion SA1. The main body portion SA1 and the flange portion SA2 are made of material that transmit light from the semiconductor device D. Moreover, a main surface SA21 and a back surface SA22 of the flange portion SA2 are mirror polished so as not to distort a light flux that is transmitted through the flange portion SA2. The shape of the flange portion SA2 can be provided as, for example, a disk shape. Although the solid immersion lens S is attached to the high-power objective lens 54b, the solid immersion lens SA is not attached to the high-power objective lens 54b, and is provided as a separate body from the high-power objective lens 54b.

The suction unit 10A has a configuration for suction fixing such a solid immersion lens SA to the second surface 14A. That is, in the second surface 14A of the main body portion 11A, a plurality of (for example, two to five) second suction grooves 14Aa for vacuum sucking the solid immersion lens SA to fix the solid immersion lens SA to the second surface 14A (particularly, light emitting surface 17A) are formed. The second suction grooves 14Aa can be formed at, for example, positions corresponding to the first suction grooves 13a, in ring shapes. Each of the second suction grooves 14Aa communicates with a suction port (not shown), and the interior thereof is vacuumed by a vacuum pump V or the like connected to the suction port. In the suction unit 10A, the solid immersion lens SA is suction fixed to the second surface 14A by vacuuming the interior of the second suction grooves 14Aa. As a result of using such a suction unit 10A, suction of the solid immersion lens SA can be performed by the whole of the flange portion SA2, so that suction fixing of the solid immersion lens SA to the second surface 14A can be reliably performed with a relatively large force.

Here, the semiconductor device observation apparatus 100 can further include a drive motor M with a linear stage. The drive motor M moves the solid immersion lens SA along the second surface 14A of the suction unit 10A under the control of the control section 70. In the semiconductor device observation apparatus 100 thus using the suction unit 10A, the solid immersion lens SA, and the drive motor M, observation of the semiconductor device D can be performed, for example, as in the following.

First, after releasing suction fixing of the solid immersion lens SA to the second surface 14A, as shown in FIG. 10(b), the solid immersion lens SA is moved along the second surface 14A of the suction unit 10A (in the arrow direction in the figure) by the drive motor M to arrange the flange portion SA2 of the solid immersion lens SA on the light emitting surface 17A of the light transmitting portion 12A (that is, to move the main body portion SA1 of the solid immersion lens SA away from the light emitting surface 17A). The interior of the second suction grooves 14Aa is vacuumed in that state to thereby suction fix the solid immersion lens SA to the second surface 14A. Then, observation of the semiconductor device D is performed by use of the low-power objective lens 54a. Observation at a low magnification is thus performed, while the semiconductor wafer W is moved relative to the light transmitting portion 12A to arrange a desired observation position of the semiconductor device D at the center of the light transmitting portion 12A.

Subsequently, after releasing suction fixing of the solid immersion lens SA to the second surface 14A, as shown in FIG. 10(a), the suction unit 10A is moved by the drive motor M to arrange the main body portion SA1 of the solid immersion lens SA on the light emitting surface 17A of the light transmitting portion 12A. The interior of the second suction grooves 14Aa is vacuumed in that state to thereby suction fix the solid immersion lens SA to the second surface 14A. Then, observation of the semiconductor device D is performed by use of the main body portion SA1 of the solid immersion lens SA and the high-power objective lens 54b. By thus performing observation by use of the hemispherical main body portion SA1 of the solid immersion lens SA, the magnification and NA in, for example, microscopic observation are both increased by 3.5 times, and high-resolution observation is enabled.

When the observation position in the semiconductor device D is moved, after releasing suction fixing of the solid immersion lens SA and moving the main body portion SA1 to above (below in the figure) a position wished to be observed, the solid immersion lens SA is suction fixed to perform observation. The observation itself may be performed at all times even during a movement of the solid immersion lens SA. Also, performing observation with the objective lens located directly above the main body portion SA1 allows observation in a wide range with the least aberration.

As described above, by the suction unit 10A, the semiconductor device D is suction fixed to the light incident surface 16A by vacuum suction using the first suction grooves 13a, while the main body portion SA1 of the solid immersion lens SA can be suction fixed to the light emitting surface 17A by vacuum suction using the second suction grooves 14Aa. Moreover, by suction fixing the semiconductor device D to the light incident surface 16A in the same manner while stopping the vacuum suction using the second suction grooves 14Aa, the suction fixing of the solid immersion lens SA can be released to move the main body portion SA1 of the solid immersion lens SA away from the light emitting surface 17A. Thus, by the suction unit 10A, the main body portion SA1 of the solid immersion lens SA can be easily moved with the semiconductor device D to serve as an observation object being suction fixed to the light incident surface 16A. Therefore, by the suction unit 10A, observation of the semiconductor device D at a low magnification using the flange portion SA2 of the solid immersion lens SA and observation of the semiconductor device D at a high magnification using the main body portion SA1 of the solid immersion lens SA can be easily changed over.

Therefore, by the semiconductor device observation apparatus 100 including the suction unit 10A, observation of the semiconductor device D at a low magnification using the flange portion SA2 of the solid immersion lens SA and the low-power objective lens 54a and observation of the semiconductor device D at a high magnification using the main body portion SA1 of the solid immersion lens SA and the high-power objective lens 54b can be easily changed over under the control of the control section 70.

[First Embodiment of Semiconductor Device Observation Method]

Figure 11:
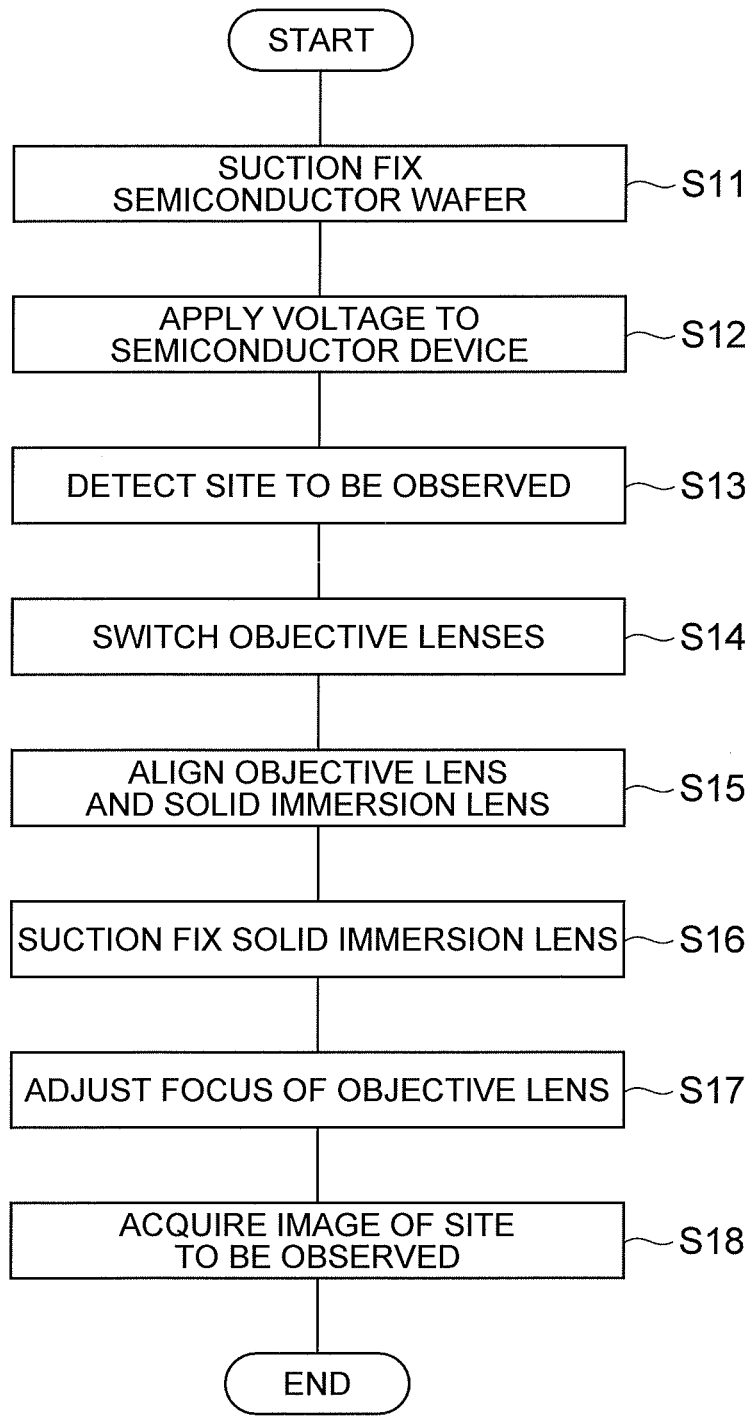
FIG. 11 is a flowchart showing steps of a first embodiment of a semiconductor device observation method according to the present invention.
Figure 12:
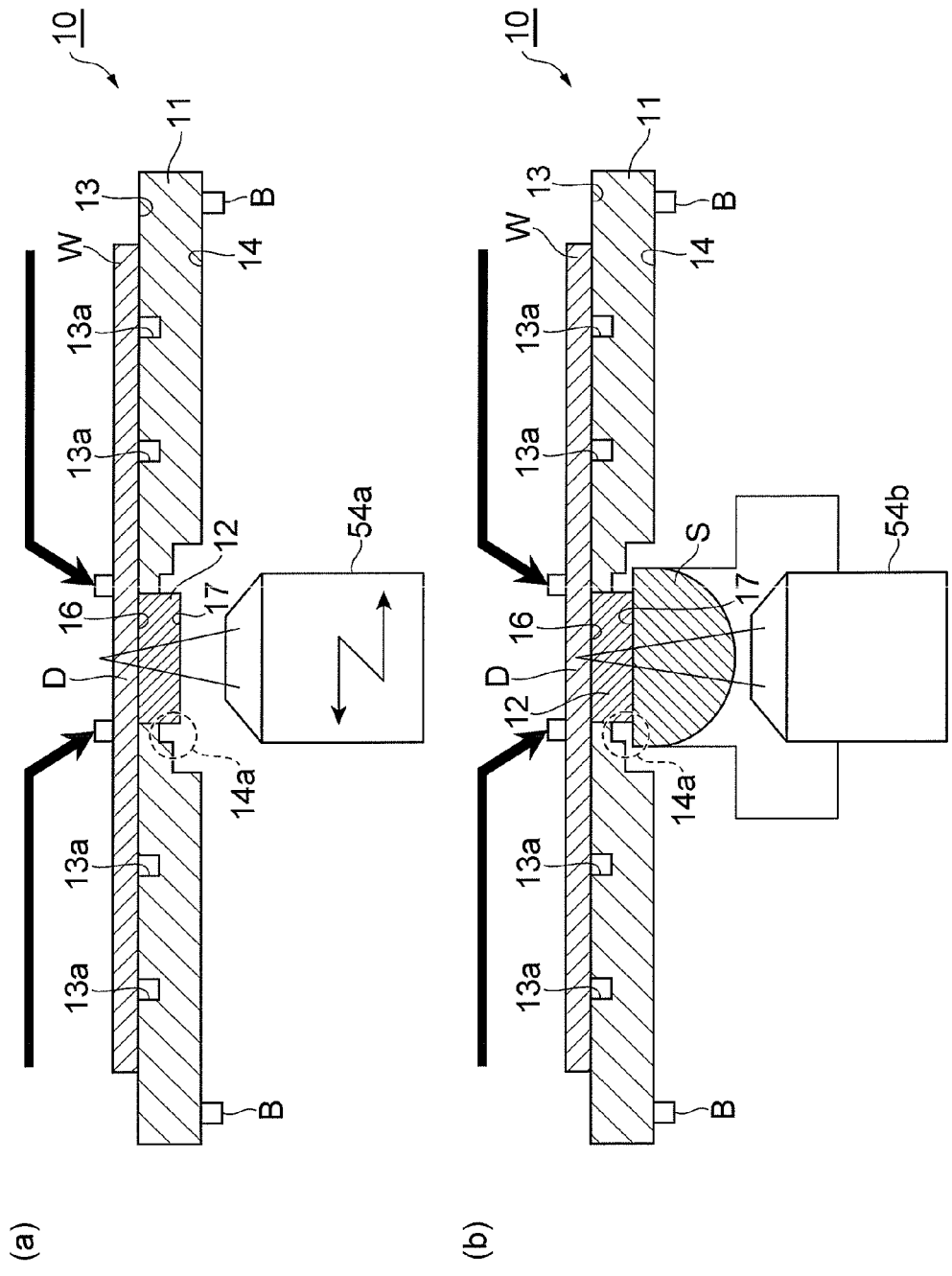
FIG. 12 are views schematically showing some steps of the first embodiment of a semiconductor device observation method according to the present invention.

Next, a first embodiment of a semiconductor device observation method according to the present invention will be described. The semiconductor device observation method according to the present embodiment is a method for observing a semiconductor device by use of the semiconductor device observation apparatus 100 described above. FIG. 11 is a flowchart showing steps of this semiconductor device observation method, and FIG. 12 are views schematically showing some steps of this semiconductor device observation method.

First, a semiconductor wafer W is vacuum sucked by use of the suction unit 10 to thereby suction fix the semiconductor wafer W to the first surface 13 (step S11). More specifically, the valve control unit 71 opens the valve E arranged between the first suction grooves 13a and the vacuum pump V to vacuum the interior of the first suction grooves 13a so as to suction fix the semiconductor wafer W to the first surface 13. At this time, the semiconductor device D formed in the semiconductor wafer W is fixed to the light incident surface 16.

Subsequently, while the semiconductor device D is fixed to the light incident surface 16, the tester 40 causes the probe pin 42 to contact a predetermined site of the semiconductor device D, and applies voltage to said predetermined site (step S12: voltage application step).

Subsequently, light emitted from the semiconductor device D due to the application of voltage in step S12 and to be transmitted through the light transmitting portion 12 is observed by use of the low-power objective lens 54a arranged on the side of the light emitting surface 17 to thereby detect a site to be observed (for example, a failure site) in the semiconductor device D (step S13: detecting step). The application of voltage to the semiconductor device D may be once stopped after this step S13 and performed again when acquiring an image of the site to be observed in step S18 to be mentioned later.

In this step S13, the stage control unit 72 controls the XYZ stage 53 to, as shown in FIG. 12(a), drive the low-power objective lens 54a in the X-Y direction to thereby adjust the positional relationship between the low-power objective lens 54a and the light transmitting portion 12, while light transmitted through the light transmitting portion 12 is observed to detect a site to be observed. In this step 13, according to necessity, a plurality of sites to be observed may be detected and their positional data in terms of the X-Y direction may be stored in the control section 70.

Subsequently, the lens turret control unit 75 controls (rotates) the lens turret 55 to thereby switch objective lenses from the low-power objective lens 54a to the high-power objective lens 54b (step S14).

Subsequently, the stage control unit 72 controls the XYZ stage 53 to move the high-power objective lens 54b and the solid immersion lens S attached to the high-power objective lens 54b in the X-Y direction on the light emitting surface 17 side so as to align these lenses with the site to be observed detected in step S13 (step S15: aligning step).

Subsequently, the solid immersion lens S is vacuum sucked to thereby suction fix the solid immersion lens S to the light emitting surface 17 (step S16: suction fixing step). More specifically, the valve control unit 71 opens the valve E arranged between the second suction groove 14a and the vacuum pump V to vacuum the interior of the second suction groove 14a so as to suction fix the solid immersion lens to the light emitting surface 17.

In this step S16, first, the stage control unit 72 controls the XYZ stage 53 to move the high-power objective lens 54b and the solid immersion lens S in the Z direction and bring the solid immersion lens S into contact with the light emitting surface 17, and then the solid immersion lens S can be fixed to the light emitting surface 17 by vacuum suction.

Subsequently, the stage control unit 72 controls the XYZ stage 53 to adjust the position in the Z direction of the high-power objective lens 54b to thereby adjust the focus position of the high-power objective lens 54b (step S17: focus adjusting step). Here, because the solid immersion lens S is held movably relative to the high-power objective lens 54b, even after the solid immersion lens S is suction fixed in step S16, the position of the high-power lens 54b can be adjusted.

Then, the detector 52 acquires an image of the site to be observed detected in step S13 by use of the high-power objective lens 54b and the solid immersion lens S as shown in FIG. 12(b) (step S18: image acquisition step). The acquired image is sent to a computer or the like connected to the detector 52 and displayed.

Thereafter, according to necessity, the suction fixing of the solid immersion lens S can be released, and the steps of step S15 onward described above can be repeatedly performed in order to acquire an image of another site to be observed.

As described above, by the semiconductor device observation method according to the present embodiment, observation of the semiconductor device D is performed by the low-power objective lens 54a without using the solid immersion lens S to detect a site to be observed, and thereafter, the solid immersion lens S is suction fixed to the light emitting surface 17, and observation of the site to be observed is performed by the high-power objective lens 54b. Thus, by this semiconductor device observation method, observation of the semiconductor device D at a low magnification without using the solid immersion lens S and observation of the semiconductor device D at a high magnification using the solid immersion lens can be easily changed over.

Moreover, in the semiconductor device observation method according to the present embodiment, voltage is applied to the semiconductor device D with the semiconductor device D suction fixed to the light incident surface 16, and the semiconductor device D is observed while the positional relationship between the low-power objective lens 54a and the suction unit 10 is adjusted. Therefore, this semiconductor device observation method can be applied when the width of the light transmitting portion 12 is relatively large to the width of the semiconductor device. Further, in such a case, because it is not necessary to change the positional relationship between the semiconductor device D and the suction unit 10 (that is, it is not necessary to align the light transmitting portion 12) when detecting a site to be observed, the site to be observed is easily identified.

[Second Embodiment of Semiconductor Device Observation Method]

Figure 13:
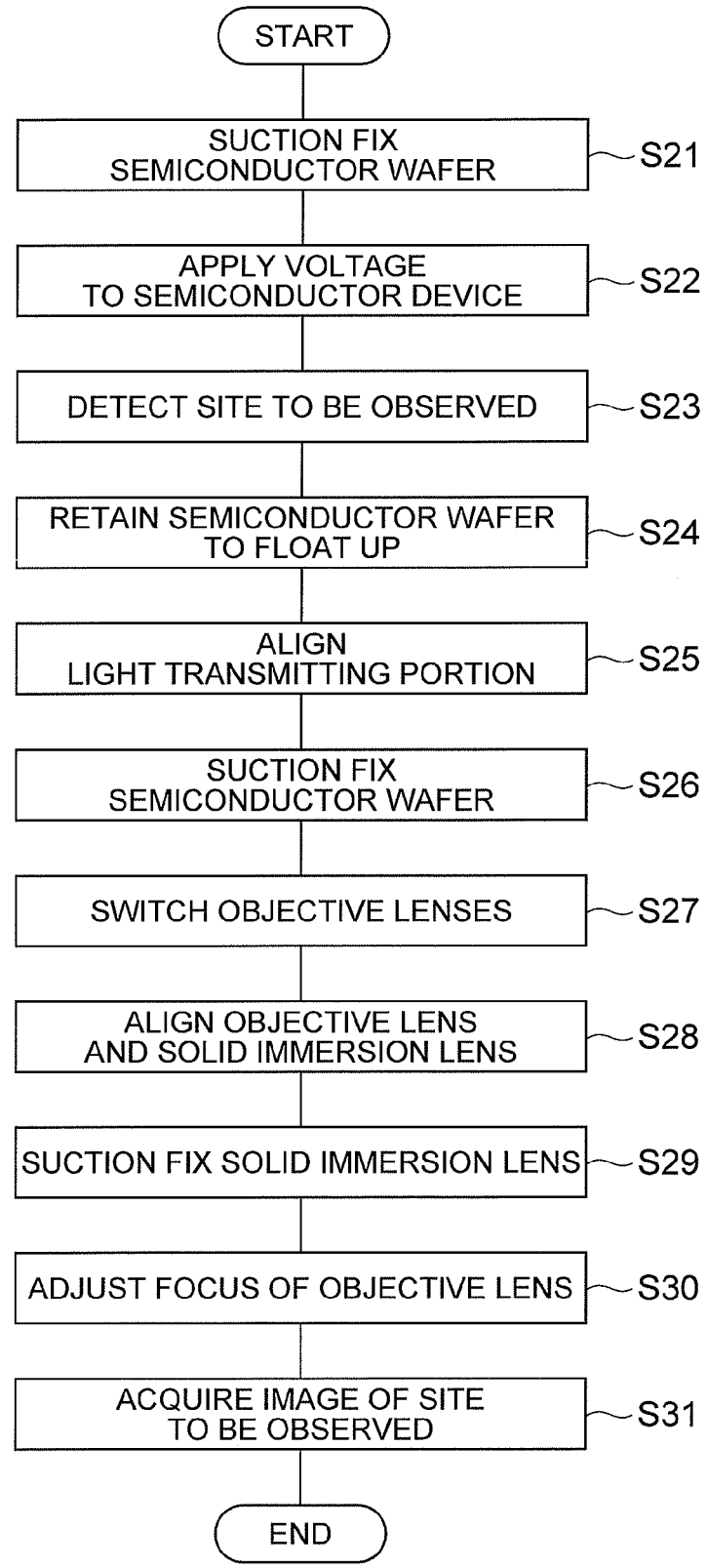
FIG. 13 is a flowchart showing steps of a second embodiment of a semiconductor device observation method according to the present invention.

Next, a second embodiment of a semiconductor device observation method according to the present invention will be described. The semiconductor device observation method according to the present embodiment is also a method for observing a semiconductor device by use of the semiconductor device observation apparatus 100 described above. FIG. 13 is a flowchart showing steps of this semiconductor device observation method, and FIG. 14 are views schematically showing some steps of this semiconductor device observation method.

First, a semiconductor wafer W is vacuum sucked by use of the suction unit 10 to thereby suction fix the semiconductor wafer W to the first surface 13 (step S21). More specifically, the valve control unit 71 opens the valve E arranged between the first suction grooves 13a and the vacuum pump V to vacuum the interior of the first suction grooves 13a so as to suction fix the semiconductor wafer W to the first surface 13. At this time, the semiconductor device D formed in the semiconductor wafer W is fixed to the light incident surface 16.

Subsequently, while the semiconductor device D is fixed to the light incident surface 16, the tester 40 causes the probe pin 42 to contact a predetermined site of the semiconductor device D, and applies voltage to said predetermined site (step S22: voltage application step).

Subsequently, light emitted from the semiconductor device D due to the application of voltage in step S22 and to be transmitted through the light transmitting portion 12 is observed by use of the low-power objective lens 54a arranged on the side of the light emitting surface 17 to thereby detect a site to be observed in the semiconductor device D (step S23: detection step). In this step S23, according to necessity, a plurality of sites to be observed may be detected and their positional data in terms of the X-Y direction may be stored in the control section 70. The application of voltage to the semiconductor device may be once stopped after this step S23 and performed again when acquiring an image of the site to be observed in step S31 to be mentioned later.

Subsequently, the semiconductor wafer W is retained to float up from the suction unit 10 by blowout of air from the suction unit 10 (step S24: suction unit moving step). More specifically, the valve control unit 71 closes the valve E arranged between the first suction grooves 13a and the vacuum pump V to stop vacuuming of the interior of the first suction grooves 13a as well as opens the valve E arranged between the first suction grooves 13a and the air compressor F to cause blowout of compressed air from the first suction grooves 13a, to thereby make the semiconductor wafer W arranged on the first surface 13 float up. Accordingly, the semiconductor wafer W is retained to float up between the first surface 13 and the probe pin 42. At this time, the semiconductor wafer W is pressed against the probe pin 42 by compressed air, and stabilized in its position in the X-Y direction. The degree of float-up of the semiconductor wafer W can be judged based on an interference pattern due to interference of reflected light from a boundary between the semiconductor wafer W and the light transmitting portion 12. This interference pattern is all one dark color at suction, but brightens as the semiconductor wafer W floats up, and fringes begin to appear.

Subsequently, as shown in FIG. 14(*a*), the chuck control unit 76 controls the suction unit drive mechanism 31 to move the suction unit 10 in the X-Y direction as well as the stage control unit 72 moves the low-power objective lens 54a in the X-Y direction, to perform alignment of the light transmitting portion 12 so that the center of the light transmitting portion 12 is aligned with the site to be observed detected in step S23 (step S25: suction unit moving step). However, in this step S25, the low-power objective lens 54a and the suction unit 10 may be kept fixed, and the semiconductor device D (semiconductor wafer W) may be moved. In this case, movement of the semiconductor wafer W is performed by use of the wafer suction fixing portion 32. Thus, in step S25, it suffices to move low-power objective lens 54a and the suction unit 10 in the X-Y direction relative to the semiconductor device D.

Moreover, in this step S25, by aligning the light transmitting portion 12 while observing a reflected image of the semiconductor device D, the center of the light transmitting portion 12 can be reliably aligned with the site to be observed. Furthermore, in this step S25, if the center of the light transmitting portion 12 is in alignment with the site to be observed can be checked, after alignment of the light transmitting portion 12, by again applying voltage to the semiconductor device D. Accordingly, the alignment accuracy of the light transmitting portion 12 can be further improved.

Subsequently, the semiconductor wafer W is vacuum sucked to thereby suction fix the semiconductor device D to the light incident surface 16 (step S26: suction unit moving step). More specifically, the valve control unit 71 closes the valve E arranged between the first suction grooves 13a and the air compressor F to stop blowout of compressed air, and further opens the valve E arranged between the first suction grooves 13a and the vacuum pump V to vacuum the interior of the first suction grooves 13a so as to suction fix the semiconductor wafer.

Subsequently, the lens turret control unit 75 controls (rotates) the lens turret 55 to thereby switch objective lenses from the low-power objective lens 54a to the high-power objective lens 54b (step S27).

Subsequently, the stage control unit 72 controls the XYZ stage 53 to move the high-power objective lens 54b and the solid immersion lens S attached to the high-power objective lens 54b in the X-Y direction on the light emitting surface 17 side so as to align these lenses with the site to be observed with which the light transmitting portion 12 is aligned (step S28: alignment step).

Subsequently, the solid immersion lens S is suction fixed to the light emitting surface 17 by vacuum suction (step S29: suction fixing step). More specifically, the valve control unit 71 opens the valve E arranged between the second suction groove 14a and the vacuum pump V to vacuum the interior of the second suction groove 14a so as to suction fix the solid immersion lens S.

In this step S29, first, the stage control unit 72 controls the XYZ stage 53 to move the high-power objective lens 54b and the solid immersion lens S in the Z direction and bring the solid immersion lens S into contact with the light emitting surface 17, and then the solid immersion lens S can be fixed to the light emitting surface 17 by vacuum suction.

Subsequently, the stage control unit 72 controls the XYZ stage 53 to adjust the position in the Z direction of the high-power objective lens 54b to thereby adjust the focus position of the high-power objective lens 54b (step S30: focus adjusting step). Here, because the solid immersion lens S is held movably relative to the high-power objective lens 54b, even after the solid immersion lens S is suction fixed in step S27, the position of the high-power objective lens 54b can be adjusted.

Then, the detector 52 acquires an image of the site to be observed by use of the high-power objective lens 54b and the solid immersion lens S as shown in FIG. 14(*b*) (step S31: image acquisition step). The acquired image is sent to a computer or the like connected to the detector 52 and displayed. Thereafter, according to necessity, the steps of step S24 onward described above can be repeatedly performed by use of the positional data stored in step S23 in order to acquire an image of another site to be observed.

As described above, by the semiconductor device observation method according to the present embodiment, similar to the semiconductor device observation method according to the above-described first embodiment, observation of the semiconductor device D at a low magnification without using the solid immersion lens S and observation of the semiconductor device D at a high magnification using the solid immersion lens can be easily changed over.

Moreover, the semiconductor device observation method according to the present embodiment is for retaining the semiconductor wafer W to float up from the suction unit 10, and moving the low-power objective lens 54a and the suction unit 10 relative to the semiconductor device D to align the light transmitting portion 12 with the site to be observed. Accordingly, this semiconductor device observation method can be applied when the width of the light transmitting portion 12 is relatively small to the width of the semiconductor device D. Further, in such a case, because the contact area between the light incident surface 16 and the semiconductor device D and the contact area between the light emitting surface 17 and the solid immersion lens S are relatively small, the suction efficiency of the semiconductor device D and the solid immersion lens S is high. Accordingly, evanescent coupling can be reliably realized between the semiconductor device D and the light transmitting portion 12 and between the light transmitting portion 12 and the solid immersion lens S.

In the semiconductor device observation method according to the present embodiment, after detecting a site to be observed in step S23, by retaining the semiconductor wafer W to float up from the suction unit 10, switching the objective lens to the high-power objective lens 54b, and integrally moving the suction unit 10, the high-power objective lens 54b, and the solid immersion lens S, the light transmitting portion 12, the high-power objective lens 54b, and the solid immersion lens S can be simultaneously aligned with the site to be observed by use of positional data stored in the control section 70. In that case, as subsequent steps, after suction fixing the solid immersion lens S and the semiconductor wafer W in step S29, step S30 and step S31 are performed. In this case, after acquiring an image of a site to be observed in step S31, by retaining the semiconductor wafer W to float up from the suction unit 10 without separating the solid immersion lens S from the suction unit 10, and integrally moving the suction unit 10, the high-power objective lens 54b, and the solid immersion lens S to simultaneously align the suction unit 10, the high-power objective lens 54b, and the solid immersion lens S with another site to be observed, the plurality of sites to be observed can be easily observed.

Moreover, the suction unit 10, semiconductor device observation apparatus 100, and semiconductor device observation methods mentioned above can be used also for acquisition of a light emission image from the semiconductor device D due to application of voltage, and can be used also for acquisition of a circuit pattern image formed in the semiconductor device D. Moreover, the suction unit 10, semiconductor device observation apparatus 100, and semiconductor device observation methods mentioned above can be used also for acquisition of a light emission image that is obtained by aligning the focal position with the observation position by use of a circuit pattern image being a reflected image from the semiconductor device D and applying voltage to the semiconductor device D and acquisition of an OBIRCH image and/or an OBIC image by laser light scanning.

INDUSTRIAL APPLICABILITY

According to the present invention, a suction unit, a semiconductor device observation apparatus, and a semiconductor device observation method which allow easily performing changeover between observation at a low magnification and observation at a high magnification of a semiconductor device can be provided.

REFERENCE SIGNS LIST 10, 10A: suction unit, 11, 11A: main body portion, 12, 12A: light transmitting portion, 13: first surface, 13a: first suction groove, 14, 14A: second surface, 14a, 14Aa: second suction groove, 15, 15A: through-hole, 16, 16A: light incident surface, 17, 17A: light emitting surface, 18: first recess portion, 18a: bottom surface, 19: second recess portion, 19a: bottom surface, 22: water cooling jacket, 40: tester, 51: light guide optical system, 52: detector, 54a: low-power objective lens, 54b: high-power objective lens, 55: lens turret.

The invention claimed is:

1. A suction unit to be used for a semiconductor device observation apparatus for performing observation of a semiconductor device by use of a solid immersion lens, comprising:
a main body portion having a first surface on which a semiconductor wafer formed with the semiconductor device is arranged and a second surface that is a surface opposite to the first surface, and in which a through-hole that penetrates through the first surface and the second surface is formed; and
a light transmitting portion having a light incident surface onto which light from the semiconductor device is made incident and a light emitting surface from which light made incident from the light incident surface is emitted, and which is fitted to the through-hole so that the light incident surface is exposed to a side of the first surface and the light emitting surface is exposed to a side of the second surface, wherein
in the first surface, a first suction groove for vacuum sucking the semiconductor wafer to fix the semiconductor device to the light incident surface is formed, and
in the second surface, a second suction groove for vacuum sucking the solid immersion lens to fix the solid immersion lens to the light emitting surface is formed.

2. The suction unit according to claim 1, wherein a recess portion to arrange the solid immersion lens is formed in the second surface,
the through-hole is formed in a bottom surface of the recess portion,
the light emitting surface is located on the second surface side further than the bottom surface of the recess portion, and
the second suction groove is formed along an edge portion of the through-hole on the bottom surface of the recess portion.

3. The suction unit according to claim 1, wherein the light transmitting portion is made of a material having substantially the same refractive index as that of a material to form a substrate of the semiconductor device.

4. The suction unit according to claim 1, further comprising cooling means for cooling the main body portion.

5. A semiconductor device observation apparatus for performing observation of a semiconductor device by use of a solid immersion lens, comprising:
the suction unit according to claim 1;
a light guide optical system for guiding light transmitted through the light transmitting portion; and
imaging means for imaging light guided by the light guide optical system.

6. The semiconductor device observation apparatus according to claim 5, wherein the light guide optical system includes a first objective lens having a predetermined magnification, a second objective lens having a magnification higher than the predetermined magnification, and objective lens switching means for switching the first objective lens and the second objective lens, and
to the second objective lens, in a manner movable in a direction along its optical axis, the solid immersion lens is attached.

7. The semiconductor device observation apparatus according to claim 5, further comprising voltage application means for applying voltage to the semiconductor device.

8. A semiconductor device observation method for observing a semiconductor device formed in a semiconductor wafer, comprising:
- a voltage application step of applying voltage to a predetermined site of the semiconductor device arranged on a light incident surface of a light transmitting portion of a suction unit;
- a detection step of detecting a site to be observed in the semiconductor device by observing light emitted from the semiconductor device and to be transmitted through the light transmitting portion by use of a first objective lens arranged on a side of a light emitting surface opposite to the light incident surface of the light transmitting portion;
- an alignment step of aligning a second objective lens having a magnification higher than that of the first objective lens and a solid immersion lens attached to the second objective lens, on the light emitting surface side, with the site to be observed detected in the detection step;
- a suction fixing step of fixing the solid immersion lens to the light emitting surface by vacuum suction;
- a focus adjusting step of adjusting a focus of the second objective lens by adjusting the position of the second objective lens in an optical axis direction of the second objective lens; and
- an image acquisition step of acquiring an image of the site to be observed by use of the second objective lens.

9. The semiconductor device observation method according to claim 8, wherein in the voltage application step, voltage is applied to the semiconductor device with the semiconductor device fixed to the light incident surface by vacuum sucking of the semiconductor wafer, and in the detection step, the site to be observed is detected by observing light from the semiconductor device while adjusting a positional relationship between the first objective lens and the light transmitting portion.

10. The semiconductor device observation method according to claim 8, further comprising, between the detection step and the alignment step, a suction unit moving step of retaining the semiconductor wafer to float up from the suction unit by blowout of air from the suction unit, moving the suction unit relative to the semiconductor device to align the light transmitting portion with the site to be observed detected in the detection step, and fixing the semiconductor device to the light incident surface by vacuum sucking the semiconductor wafer, wherein in the alignment step, the second objective lens and the solid immersion lens are aligned with the site to be observed with which the light transmitting portion is aligned.

11. The semiconductor device observation method according to claim 8, wherein in the alignment step, by retaining the semiconductor wafer to float up from the suction unit by blowout of air from the suction unit, and integrally moving the suction unit, the second objective lens, and the solid immersion lens, the suction unit, the second objective lens, and the solid immersion lens are aligned with the site to be observed.

12. The semiconductor device observation method according to claim 8, wherein in the suction fixing step, after bringing the solid immersion lens into contact with the light emitting surface by moving the solid immersion lens in the optical axis direction of the second objective lens, the solid immersion lens is fixed to the light emitting surface by vacuum suction.

* * * * *